US007901920B2

(12) United States Patent
Huckriede et al.

(10) Patent No.: US 7,901,920 B2
(45) Date of Patent: Mar. 8, 2011

(54) VIROSOME-LIKE-PARTICLES

(75) Inventors: Anke Luise Wilhelmine Huckriede, Haren (NL); Jørgen Martin de Jonge, Groningen (NL); Antonius Johannes Hendrikus Stegmann, Katwijk (NL); Pieter Joseph Schoen, Groningen (NL); Jan Christiaan Wilschut, Garnwerd (NL)

(73) Assignee: Bestewil Holding B.V., Amsterdam (NL)

( * ) Notice: Subject to any disclaimer, the term of this patent is extended or adjusted under 35 U.S.C. 154(b) by 0 days.

(21) Appl. No.: 10/544,939

(22) PCT Filed: Feb. 11, 2004

(86) PCT No.: PCT/NL2004/000101
§ 371 (c)(1),
(2), (4) Date: Mar. 24, 2006

(87) PCT Pub. No.: WO2004/071492
PCT Pub. Date: Aug. 26, 2004

(65) Prior Publication Data
US 2006/0228376 A1 Oct. 12, 2006

(30) Foreign Application Priority Data
Feb. 13, 2003 (EP) .................................. 03075422

(51) Int. Cl.
*C12N 7/04* (2006.01)
*A61K 9/127* (2006.01)
*A61K 39/12* (2006.01)
*A61K 39/145* (2006.01)
*A61K 39/295* (2006.01)

(52) U.S. Cl. .................. 435/236; 424/202.1; 424/204.1; 424/210.1; 424/450

(58) Field of Classification Search .................. 435/236; 424/202.1, 204.1, 210.1, 450
See application file for complete search history.

(56) References Cited

U.S. PATENT DOCUMENTS
5,252,348 A * 10/1993 Schreier et al. ............... 424/450
7,037,499 B1 * 5/2006 Glenn et al. ............... 424/184.1
2001/0034432 A1 * 10/2001 Sodroski et al. ............. 530/350

FOREIGN PATENT DOCUMENTS
EP 0231039 8/1987
WO WO9206677 4/1992
WO WO9213525 8/1992

OTHER PUBLICATIONS

Molecular Biology of the Cell, Third Edition, Alberts et al., Garland Publishing, 1994.*
Hauser, Biochimica et Biophysica Acta 1508(1-2):164-181, 2000.*
Johnson et al, J. Virology 52(1): 238-247, 1984.*
Waelti et al, Cancer Research 62(2):437-444, 2002; available online Jan. 15.*
Conne et al, Vaccine 15(15): 1675-1679, 1997.*
Kessi et al, Biochemistry 33:10825-10836, 1994.*
Gabriel et al, Biochemistry 26: 2432-2440, 1987; p. 2432 only.*
Gluck et al, J. Clin. Invest. 90:2491-2495, 1992.*
Withoff et al, Gene Therapy 8:1515-1523, 2001.*
Markgraf et al, Cloning 3(1):11-21, 2001.*
Hunziker et al, Molecular Immunology 38(6): 475-484, 2001.*
Rubin et al, Nutrition 16: 95-100, 2000; p. 95 only.*
Helenius et al, Eur. J. Biochem. 116:27-35, 1981.*
Spivak et al, Biochem J. 252:275-281, 1988.*
Stegmann, Toon et al., "Functional Reconstitution of Influenza Virus Envelopes", *The EMBO Journal*, vol. 6, No. 9, pp. 2651-2659 (1987).
Hughson, Frederick M., "Enveloped Viruses: A Common Mode of Membrane Fusion?" *Current Biology*, 7:R565-R569 (1997).
Kim, Hong Sung, et al., "Effect of Lipid Compositions on Gene Transfer into 293 Cells Using Sendai F/HN-Virosomes", *Journal of Biochemistry and Molecular Biolog*, 35(5):459-464 (2002).
Markgraf, Karin, et al., "Lipid Composition of Virosomes Modulates Their Fusion Efficiency with Cryopreserved Bull Sperm Cells", *Cloning*, 3(1):11-21 (2001).
Kaneda, Yasufumi, "Virosomes: Evolution of the Liposome as a Targeted Drug Delivery System", *Elsevier Science B.V.*, (2000) 197-205.
Scheiffele et al., "Influenza viruses select ordered lipid domains during budding from the plasma membrane," J Biol Chem. Jan. 22, 1999;274(4):2038-44.
Collen, Anna, et al., "A novel two-step extraction method with detergent/polymer systems for primary recovery of the fusion protein endoglucanase I-hydrophobin I", Biochimica et Biophysica Acta 1569 (2002) pp. 139-150, Elsevier.
Longo, Marjorie L, et al., "Interaction of the Influenza Hemagglutinin Fusion Peptide with Lipid Bilayers: Area Expansion and Permeation", Biophysical Journal, vol. 73, Sep. 1997, pp. 1430-1439, Biophysical Society.
Paternostre, M. et al., "Solubilization and Reconstitution of Vesicular Stomatitis Virus Envelope Using Octylglucoside", Biophysical Journal, vol. 72, Apr. 1997, pp. 1683-1694, The Biophysical Society.
Eidelman, Ofer, et al., "pH-dependent Fusion Induced by Vesicular Stomatitis Virus Glycoprotein Reconstituted into Phospholipid Vesicles", The Journal of Biological Chemistry, vol. 259, Apr. 1984, pp. 4622-4628.

(Continued)

*Primary Examiner* — Kevin K. Hill
(74) *Attorney, Agent, or Firm* — Hoffmann & Baron, LLP

(57) ABSTRACT

The invention relates to the production of virosome-like-particles. The invention provides a method for producing a virosome-like-particle comprising contacting an enveloped virus with a solution containing a short-chain phospholipid allowing solubilisation of the viral envelope of said virus further comprising removing short-chain phospholipid from said solution allowing formation of a functionally reconstituted viral envelope.

12 Claims, 5 Drawing Sheets

OTHER PUBLICATIONS

Figure 1:
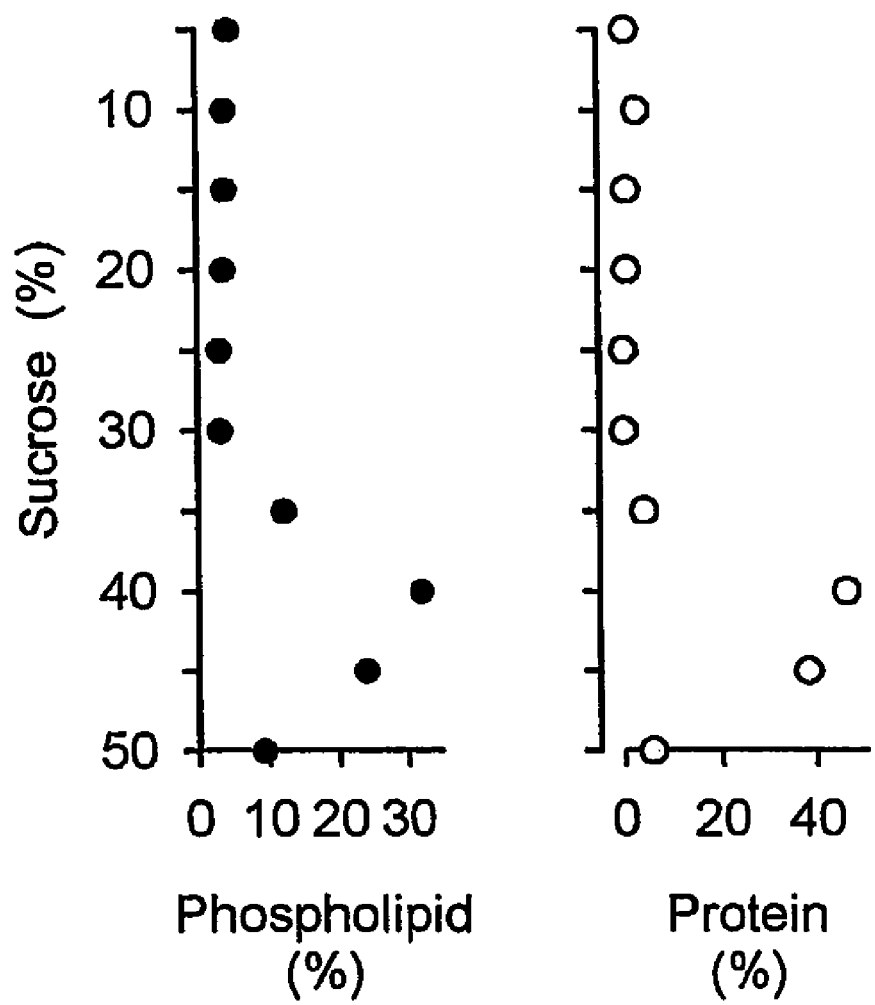

Nieva, Jose Luis, et al., "Membrane Fusion of Semliki Forest virus requires sphingolipids in the target membrane", The EMBO Journal, vol. 13, No. 12, pp. 2797-2804, 1994, Oxford University Press.

Shu, Wei, et al., "Interactions between HIV-1 gp41 Core and Detergents and Their Implications for Membrane Fusion", The Journal of Biological Chemistry, vol. 275, No. 3, Jan. 2000, pp. 1839-1845, The American Society for Biochemistry and Molecular Biology Inc.

Kragh-Hansen, Ulrich, et al., "The mechanism of detergent Solubilization of Liposomes and Protein-Containing Membranes", Biophysical Journal, vol. 75, Dec. 1998, pp. 2932-2946, The Biophysical Society.

Paternostre, Marie-Therese, et al., "pH-dependent fusion of reconstituted vesicular stomatitis virus envelopes with vero cells; Measurement by dequenching of fluorescence", Federation of European Biochemical Societies, vol. 243, No. 2, pp. 251-258, Jan. 1989, Elsevier.

Huckriede, Anke, et al., "The virosome concept for influenza vaccines", Science Direct, Vaccine 23S1 (2005), S1/26-S1/38, Elsevier.

Nussbaum, Ofer, et al., "Reconstitution of Functional Influenza Virus Envelopes and Fusion with Membranes and Liposomes Lacking Virus Receptors", Journal of Virology, Jul. 1987, vol. 61, No. 7, pp. 2245-2252, American Society for Microbiology.

Seddon, Annela M., et al., "Membrane proteins, lipids and detergents: not just a soap opera", Science Direct, Biochimica et Biophysica Acta 1666 (2004) pp. 105-117, Elsevier B.V.

Arnold, Thomas et al., "The Use of Detergents to Purify Membrane Proteins", Current Protocols in Protein Science, 4.8.1-4, 8.30, Aug. 2008, John Wiley & Sons, Inc.

Lapidot, Moshe, et al., "Fusion of Membrane Vesicles Bearing Only the Influenza Hemagglutinin with Erythrocytes, Living Cultured Cells, and Liposomes", The Journal of Biological Chemistry, vol. 262, No. 28, Oct. 1987, pp. 13736-13741, The American Society for Biochemistry and Molecular Biology, Inc.

Ollivon, Michel, et al., "Vesicle reconstitution from lipid-detergent mixed micelles", Biochimica et Biophysica Acta 1508 (2000) 34-50, Elsevier.

Weissman, Allan M., "Solubilization of Cellular Proteins; Solubilization of Lymphocytes", Current Protocols in Immunology, (2003) 8.1A.1-8.1A.9, John Wiley & Sons, Inc.

Blumenthal, Robert et al., "Reconstituted viral envelopes—'Trojan Horses' for drug delivery and gene therapy?", Tibtech, Feb. 1991, vol. 9, pp. 41-45, Elsevier.

Le Maire, Marc, et al., "Interaction of membrane proteins and lipids with solubilizing detergents", Biochimica et Biophysica Acta 1508 (2000) pp. 86-111, Elsevier.

Schimerlik, Michael I., "Overview of Membrane Protein Solubilization", Current Protocols in Neuroscience (1998), 5.9.1-1.5.9.5, John Wiley & Sons, Inc.

* cited by examiner

VIROSOME-LIKE-PARTICLES

This application is the U.S. National Phase of International Application No. PCT/NL2004/000101 filed on 11 Feb. 2004, which is incorporated herein by reference.

BACKGROUND OF THE INVENTION

The invention relates to the production of virosome-like-particles.

Vaccines against membrane-containing (enveloped) viruses mostly consist of killed or live attenuated viruses, or a preparation of their proteins (e.g. split virus vaccines or subunit preparations). Vaccination with killed viruses and protein preparations is safer than vaccination with live attenuated viruses, because the latter may mutate or revert back to wild-type virus. Subunit vaccines have the clear advantage that they can be prepared from viral proteins expressed by cells rather than from virus, making production safer and eliminating the risk of contaminating vaccine preparations with live viruses. However, while the injection of live viruses generally induces a strong immune response, protecting against future infections by the virus, protein preparations may fail to do so. This is because live attenuated viruses infect cells of the body, and will be replicated by these cells to some extent, after which the infected cells and viruses are detected by cells of the immune system, triggering an immune response. Live or killed viruses can also be taken up by specialized phagocytic cells of the immune system, such as dendritic cells, and be presented to other cells of the immune system, triggering an immune responses. These phagocytic cells patrol the body, ingesting particles of the size of viruses all the time, but they do not efficiently take up the purified proteins of split virus or subunit vaccines [1-2].

Numerous attempts to reinforce the immune response to subunit preparations by physical or chemical means have been undertaken. The most important principle that emerges from these experiments is that multiple copies of the viral proteins need to be combined in particles, that will be taken up efficiently by phagocytic cells. These particles can be virosome-like-particles, whole virosomes, Immune-Stimulating Complexes (ISCOMs), proteosome preparations or proteins on microparticle carriers. Frequently, these particles also contain chemical substances that are meant to stimulate the immune system (called adjuvants), which address specific receptors on the phagocytes or the effector cells of the immune system.

For example, ISCOMs are cage-like particles containing viral proteins complexed with adjuvants such as saponins like Quil A®), usually isolated from the bark of *Quillaia sopanaria* Molina. Mixed with antigen, and lipids such as cholesterol, these adjuvants form the typical ISCOM structures of between 30-40 nm, rendering the antigen sufficiently particulate for uptake by phagocytic cells of the immune system, while acting at the same time as an adjuvant. However, although ISCOMs have been used in a number of veterinary vaccines, and strongly enhance the immunogenicity of the viral membrane proteins, the development of such vaccines for humans has been inhibited by concerns about their toxicity and the complexity of the mixture [3]. A more recent type of particle, proteosomes (US application 0010053368) [4], consists of complexes of antigenic proteins such as the influenza hemagglutinin or the human immunodeficiency virus envelope glycoprotein, mixed with the purified outer membrane proteins of bacteria such as meningococci. While these multiple bacterial proteins may act as adjuvants, the complex nature of such mixtures, consisting of multiple proteins, lipids and other substances, will present a regulatory issue. Moreover, the immune response is directed against all proteins and other antigens present in the solution, and less specifically against the viral proteins.

A particularly useful kind of vaccine composition which has been developed in the art is known as 'virosomes', which are lipid bilayers containing viral glycoproteins derived from enveloped viruses. The concept of using such virosomes for vaccination purposes, particularly for vaccination against influenza, has been introduced by Almeida et al. [5]. Virosomes (or virosome-like-particles, considering that the exact size and shape of the particles is less important than that their particulate nature and functional and biologically-relevant membrane fusion activity is retained) are generally produced by extraction of membrane proteins and lipids from enveloped viruses with a detergent, followed by removal of this detergent from the extracted lipids and viral membrane proteins, in fact reconstituting or reforming the characteristic lipid bilayers (envelopes) that surround the viral core or nucleocapsid [5].

Influenza virus and Semliki Forest virus (SFV) are two classical examples of enveloped viruses. The first step in infection of cells by these viruses is uptake of intact viral particles by receptor-mediated endocytosis. Inside the endosomal compartment the conditions are mildly acidic due to the activity of a membranous ATP-dependent proton pump. Under these conditions (pH 5-6), the viral spike proteins undergo a conformational change which results in triggering of viral membrane fusion activity. Subsequent fusion of the viral membrane with that of the endosome results in cytoplasmic penetration of the viral genome, and the cell can be considered infected [6].

Enveloped viruses in general carry specific membrane proteins (the "spikes") which are required for binding to and entry of cells. For example, influenza virus carries about 500 copies of hemagglutinin (HA), which is composed of two disulfide-linked subunits, HA1 and HA2, and which forms trimers in the viral membrane [7]. The HA1 subunits form the top domain of the spike and carry a pocket responsible for binding of the virus to its plasma membrane receptor, sialylated lipids (gangliosides) and proteins. The stem region of the spike is mainly composed of the three HA2 subunits. Each HA2 subunit contains a N-terminal fusion peptide, a highly conserved apolar sequence. Upon the conformational change induced by exposure to mildly acidic pH these peptides interact with the target membrane leading to fusion [6].

While both SFV and influenza enter cells through receptor-mediated endocytosis and fusion from within acidic endosomes, the molecular mechanisms of membrane fusion mediated by SFV and influenza virus are quite different. Each Semliki Forest virion contains 80 spikes, which are each composed of three E1/E2 heterodimers [8]. These two membrane proteins have separate functions during the viral life cycle. Thus, while E2 is involved in virus-receptor binding, E1 mediates the merging of the viral and endosomal membranes. After acidification the E1/E2 complex dissociates and E1 rearranges to form homotrimers, and while influenza HA has a well-defined N-terminal fusion peptide, E1 does not. Another prominent difference between both viruses is that HA-mediated fusion is not very sensitive to target membrane lipid composition [9]. Fusion of SFV has a strict requirement for the presence of cholesterol [11-12] and sphingolipid [13-17] in the target membrane.

An essential feature of virosome-like-particles obtained by reconstitution (herein also called virosomes) is that they are particles of the size that is efficiently taken up by phagocytic cells of the immune system, and they closely mimic the composition, surface architecture and functional activities of the native viral envelope. Virosomes that are particularly active in inducing an immune response were found to have maintained the proper functions of the envelope proteins of the native virus, such as membrane fusion, receptor-binding and other activities. Preservation of receptor-binding and membrane fusion activity is essential for expression of full immunogenic properties of said virosomes.

In the process used for the formation of virosomes, the viral membrane (envelope) is reformed during detergent removal. This step is thought to be necessary for a functional reconstitution of the native viral envelope, but quite difficult to control. Current detergent removal protocols that result in reconstitution are mostly based on detergents with a low critical micelle concentration (cmc), and such detergents are particularly difficult to remove, in contrast to detergents with a comparatively high cmc, which can be removed by dialysis or ultrafiltration. However, it was found that the latter type of detergent does not generally properly reconstitute viral membrane proteins, including the influenza virus hemagglutinin, leading predominantly to the formation of empty membranes on the one hand, and protein aggregates on the other.

Previously we have developed a method for the reconstitution of influenza virus HA [17,18]. This method is based on solubilisation of the virus membrane with the nonionic detergent octaethyleneglycol-n-dodecyl monoether (C12E8), and, after sedimentation of the viral nucleocapsid by ultracentrifugation, removal of the detergent from the supernatant by a hydrophobic resin (Bio-Beads SM-2). The vesicles formed in this manner have been identified as virosomes. The approach allows the introduction of reporter molecules in either the lipid bilayer or the aqueous interior of the virosomes. For this purpose, we have used a fluorescent lipid, pyrene-labeled phosphatidylcholine (pyrPC), incorporated in the virosome membrane during reconstitution, to quantitatively measure membrane fusion between virosomes and erythrocyte ghosts [18-20] or target liposomes [21]. In addition, we have encapsulated water-soluble reporter molecules, gelonin [22] and the A chain of Diphtheria toxin [18,23], in virosomes and delivered these substances to target cell cytosol. These studies, and later studies in WO 92/19267 have indicated that after C12E8-mediated reconstitution influenza virus HA has substantially retained its original activity. It is, however, well recognized that, although such virosomes can elicit strong, protective, immune responses (e.g. WO 88/08718 and WO 92/19267), alternative methods are required that allow the efficient production of functionally reconstituted viral envelopes on an industrial scale. However, removal of detergent from the supernatant by a hydrophobic resin can hardly be scaled up sufficiently.

Retention of biologically-relevant fusion activity represents the only rigorous criterion for the functional reconstitution of viral envelopes. So far, the use of detergents like C12E8 and Triton X-100, which have a low critical micelle concentration (cmc), appear to represent the method of choice for the functional reconstitution of viral envelopes [18]. However, the use of low-cmc detergents has a disadvantage in that they cannot be readily removed by dialysis. For this reason, many reconstitution procedures rely on the use of detergents with a relatively high cmc. A widely used detergent in this category is the nonionic n-octyl-β-D-glucopyranoside, or octylglucoside, which has a cmc of about 20-25 mM. In most hands, e.g. ours and in WO 92/19267, however, attempts to reconstitute HA from octylglucoside-solubilised virus were unsuccesful in a variety of conditions, and no substantially fusogenic particles were obtained [17, 18].

SUMMARY OF THE INVENTION

The invention provides a method for producing a virosome-like-particle comprising contacting an enveloped virus with a solution containing a short-chain phospholipid allowing solubilisation of the viral envelope of said virus further comprising removing the short-chain phospholipid from said solution allowing formation of a functionally reconstituted viral envelope. The method is based on the use of a short-chain lecithin (phosphatidylcholine), which is well removable by dialysis. The membrane-fusion activities of the reconstituted viral envelopes (virosomes) corresponded well to the pH-dependent fusion characteristics of the intact viruses, and to those of virosomes prepared with C12E8. This novel method of virosome preparation by gentle dialysis-mediated phospholipid removal will be especially useful for the further development of virosomes as fusogenic carrier systems. It is possible to use any of a variety of enveloped viruses, such as there are, Retroviridae such as Human Immunodeficiency virus (HIV); rubellavirus; paramyxoviridae such as parainfluenza viruses, measles, mumps, respiratory syncytial virus, human metapneumovirus; flaviviridae such as yellow fever virus, dengue virus, Hepatitis C Virus (HCV), Japanese Encephalitis Virus (JEV), tick-borne encephalitis, St. Louis encephalitis or West Nile virus; Herpesviridae such as Herpes Simplex virus, cytomegalovirus, Epstein-Barr virus; Bunyaviridae; Arenaviridae; Hantaviridae such as Hantaan; Coronaviridae; Papovaviridae such as human Papillomavirus; Rhabdoviridae such as rabies virus. Coronaviridae such as human coronavirus; Alphaviridae, Arteriviridae, filoviridae such as Ebolavirus, Arenaviridae, poxyiridae such as smallpox virus, or African Swine Fever virus, in the method as provided herein. In the detailed description we have demonstrated that the major membrane proteins of enveloped viruses, as exemplified by influenza virus and SFV, are efficiently solubilised and reconstituted with a short-chain phospholipid, as long as it has a critical micelle concentratin (CMC) that is higher than 0.1 mM, such as with 1,2-diheptanoyl-sn-phosphatidylcholine (DHPC) or 1,2-dicaproyl-sn-phosphatidylcholine (DCPC). The membrane fusion activities of the reconstituted viral envelopes corresponded well to the pH-dependent fusion characteristics of the intact viruses, showing that short-chain phospholipids functionally reconstitute envelope proteins such as HA and E1/E2. These virosome-like-particles also appear comparable to virosomes prepared with C12E8 by a method previously developed in our laboratory. The membrane fusion activity demonstrated here was based on lipid mixing of the membrane fluorophore pyrPC. This fluorophore was incorporated into the virosomal membrane during reconstitution; other amphipathic molecules may be incorporated in the same manner.

In a preferred embodiment, the method further comprises removal of viral nucleocapsid from the virus solubilized by the short-chain phospholipid, e.g. by centrifugation. Said short-chain phospholipid is preferably removed by dialysis or filtration. It is preferred that said phospholipid is a short-chain phosphatidylcholine, e.g. with a critical micelle concentration (cmc) of larger than 0.1 mM, preferably larger than 1 mM. Preferred short-chain phospholipids according to the invention are 1,2-diheptanoyl-sn-phosphatidylcholine (DHPC) or 1,2-dicaproyl-sn-phosphatidylcholine. DHPC is structurally a phospholipid, but its short fatty-acyl chains of seven carbon atoms render it more water-soluble than other phospholipids. The cmc of such molecules increases as the length of the fatty-acyl chains decrease [24]. Thus while dinonanoyl-phosphatidylcholine has a cmc of about 0.03 mM, the cmc values of dicapryloyl-phosphatidylcholine, DHPC, and DCPC are about 0.3, 2 and 14 mM, respectively.

In another embodiment the invention provides a method further comprising addition of a molecule that is not derived from said virus to said virosome-like-particle. Such a molecule may be delivered to the cell that takes up the virosome-like-particle, and may for example be a nucleic acid, a lipid or a protein, preferably derived from a pathogen, such as a virus, a bacterium or a parasite, or a tumor-specific molecule. When said molecule is of an amphiphilic nature, it will in general be presented within the context of the membrane of the virosome-like-particle. The invention also provides a virosome-like-particle obtainable by a method as provided herein, in particular for the production of a pharmaceutical composition, such as a vaccine. Such a vaccine is suitable for parenteral or mucosal application. A pharmaceutical composition comprising a virosome-like-particle according to the invention can also be used as delivery vehicle for nucleic acid or proteins. This novel method of virosome preparation by gentle dialysis-mediated phospholipid removal is especially of importance for the further use of virosome-like-particles as fusogenic carrier systems.

Here we demonstrate that the spikes of influenza virus and SFV can be efficiently solubilised and reconstituted with a short-chain phospholipid, such as DHPC or DCPC, by dialysis. Our results show that we found a new method for the reconstitution of viral envelope proteins, such as HA and E1/E2, and that the membrane fusion activities of the reconstituted viral envelopes corresponded well to the fusion characteristics of the intact viruses.

LIST OF FIGURES

FIG. 1 Sucrose gradient analysis of influenza virosome-like particles

Phospholipid (●) and protein (○) concentrations after ultracentrifuge gradient analysis of influenza virosome-like-particles as described in Example 1.

Figure 2:

FIG. 2 Electron micrograph of influenza virosome-like particle.

Negative stain (ammonium molybdate) electron micrograph of influenza virosome-like-particles; bar 100 nm.

Figure 3:
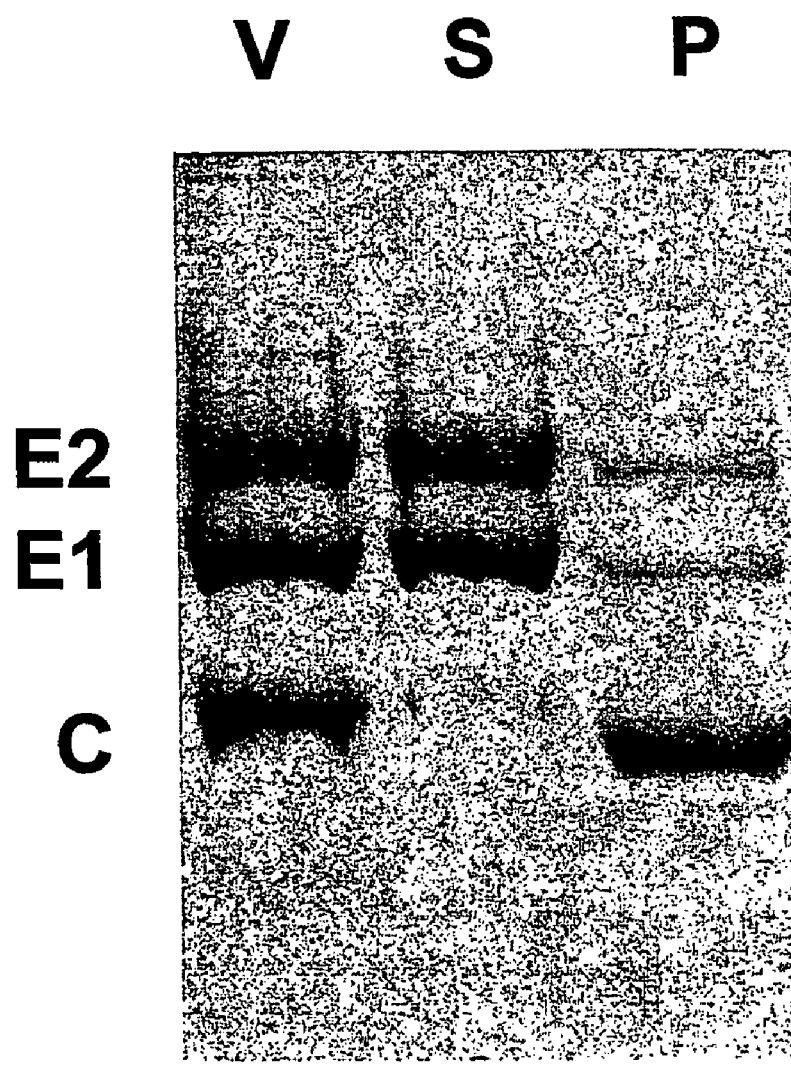

FIG. 3 DCPC-mediated solubilisation of Semliki Forest virus

Virus was mixed with DCPC, and subjected to ultracentrifugation. Aliquots of the unseparated virus (V), the supernatant (S) and the pellet (P) were subjected to polyacrylamide gelelectrophoresis in the presence of SDS. Protein bands corresponding to the E1 and E2 spike proteins and the capsid protein (C) are indicated.

Figure 4:
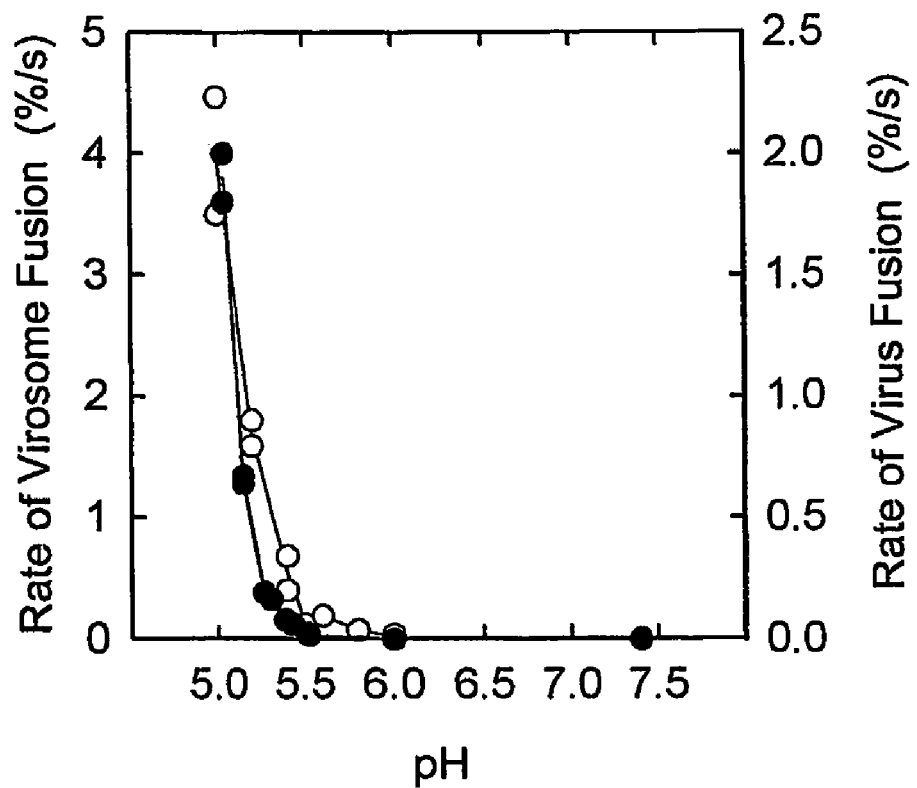

FIG. 4 Rates of fusion of intact influenza virus (●) and of DCPC-reconstituted influenza virus envelopes (○) with erythrocyte target membranes R18-labeled virus or pyrPC-labeled DCPC-reconstituted envelopes were mixed with erythrocyte ghosts at neutral pH at 37° C. At time 0 the medium was acidified to the pH value indicated. Fusion was continuously monitored by following R18 dequenching or decrease of pyrene excimer fluorescence. Rates of fusion were obtained from the fusion curves by determining the slopes of the tangents to the initial parts of the curves.

Figure 5:
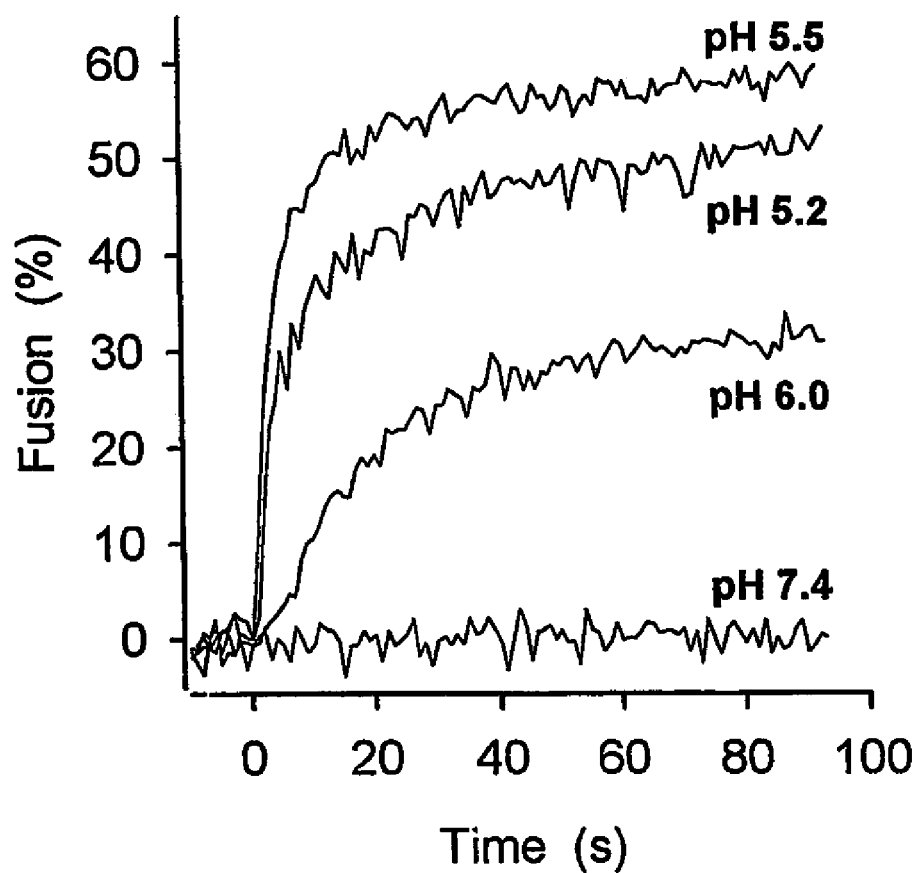

FIG. 5 Fusion of Semliki Forest DCPC virosomes with target liposomes

Reconstituted envelopes were mixed with target liposomes at neutral pH (pH 7.4) at 37° C. At time 0 the medium was acidified to the pH values indicated. Fusion was continuously monitored by following the decrease of pyrene excimer fluorescence.

DETAILED DESCRIPTION OF THE INVENTION

The present invention provides an alternative method allowing upscaling of virosome-like-particle production. Instead of using a detergent to solubilize the viral membrane and detergent removal with a hydrophobic resin to reform the envelope of a virus preparation, a short-chain phospholipid is used in these steps, facilitating production of functionally reconstituted virosome-like-particles at an industrial scale.

Virosome-like-particles are produced by solubilization of viral membranes by short-chain phospholipids and purification of the viral membrane components, followed by removal of the short-chain phospholipids. Short-chain phospholipids contain acyl chains with less than twelve carbon atoms each. In one embodiment of the invention said short-chain phospholipid is a phosphatidylcholine. In more preferred aspect of the invention, said short-chain phospholipid is 1,2-diheptanoyl-sn-phosphatidylcholine (DHPC) or 1,2-dicaproyl-sn-phosphatidylcholine (DCPC). In another preferred aspect of the invention, said short-chain phospholipid is produced synthetically or semi-synthetically. This is in marked contrast to Kim Hong Sung et al. reporting the preparation of Sendai virosomes by the classical detergent-dialysis method using various different compositions of naturally occurring (i.e. medium-chain to long-chain) phospholipids (J. Biochemistry and Molecular Biology, Vol. 35, No. 5 2002, pp 459-464. For example, phospholipids used by Kim Hong Sung et al. were egg PC, having primarily C16 and C18 fatty acyl chains, and dioleoyl-PE, having two C18:1 fatty acyl chains.

An important aspect of the present invention is that the virosome-like-particles of the present invention can be applied for vaccination with antigens that would not normally elicit a sufficient immune response, if they were not present in the membrane of virosome-like-particles. A sufficient immune response in the treated subject is a response that protects against subsequent infection by the pathogenic organism comprising the antigen. The antigens that are part of the virosome according to the invention should have a hydrophobic part that is embedded in the lipid bilayer membrane of the virosome particle. Many pathogenic entities such as viruses, bacteria, yeasts and parasites carry in their capsid, cell wall or membrane, proteins that elicit an immune response in the host. Examples of antigens that have hydrophobic elements and that are suited to be part of a virosome according to the invention are proteins present in the membrane (also called envelope in the case of viruses) of the pathogen. Therefore, in one embodiment, the antigen present in the virosome of the invention is an integral membrane protein. In preferred embodiments, said antigens are derived from a virus, a parasite, a bacterium or a tumor cell. Especially preferred are virosome-like-particles, wherein said antigen is derived from influenza virus or an alphavirus such as Semliki Forest virus (SFV). Proteins from influenza virus that can be used in virosome-like-particles of the present invention are preferably the hemagglutinin (HA) protein, the neuraminidase (NA) protein and/or the M2 protein, alone or in combination, and those from SFV that can be applied are the spike proteins E1 and E2, preferably in combination.

Viruses that can be applied and used in the formation of the virosome-like-particles according to the invention can be derived from all sorts of viruses, non-limiting examples of such viruses being: Retroviridae such as Human Immunodeficiency virus (HIV); rubellavirus; paramyxoviridae such as parainfluenza viruses, measles, mumps, respiratory syncytial virus, human metapneumovirus; flaviviridae such as yellow fever virus, dengue virus, Hepatitis C Virus (HCV), Japanese Encephalitis Virus (JEV), tick-borne encephalitis, St. Louis encephalitis or West Nile virus; Herpesviridae such as Herpes Simplex virus, cytomegalovirus, Epstein-Barr virus; Bunyaviridae; Arenaviridae; Hantaviridae such as Hantaan; Coronaviridae; Papovaviridae such as human Papillomavirus; Rhabdoviridae such as rabies virus. Coronaviridae such as human coronavirus; Alphaviridae, Arteriviridae, filoviridae such as Ebolavirus, Arenaviridae, poxyiridae such as smallpox virus, and African Swine Fever virus.

Although vaccination is generally applied for the prophylactic protection against pathogens or for the treatment of diseases following pathogenic infection, the person skilled in the art is also aware of the application of some vaccines for tumor treatment and the therapeutic use of vaccines. Moreover, an increasing number of tumor-specific proteins are found to be proper entities that can be targeted by human or humanized antibodies. Such tumor-specific proteins are also within the scope of the present invention. Many tumor-specific antigens are known in the art. Therefore, in one preferred embodiment, the present invention provides virosome-like-particles comprising a tumor-specific antigen.

In another aspect, the present invention provides a method for producing a virosome, comprising some or all of the following steps: i) dissolving the virus in a short-chain phospholipid ii) removing the viral genetic material and core proteins and iii) removing the short-chain phospholipid under conditions that allow reformation of the membrane. Preferably, the method for producing a virosome disclosed by the present invention also comprises the step of purifying said virosome.

The present invention provides a pharmaceutical preparation comprising a virosome according to the invention, and a therapeutically acceptable carrier. Therapeutically acceptable carriers for delivery are exemplified by water, buffered saline solutions, glycerin, and polysorbate 20, and may be buffered to provide a neutral pH environment.

Furthermore, the present invention provides the use of a virosome according to the invention, or a pharmaceutical preparation according to the invention, in therapy, prophylaxis or diagnosis. Preferably the pharmaceutical preparation according to the invention is used for parenteral delivery. In another preferred embodiment, the pharmaceutical preparation according to the invention is used for oral delivery, and in yet another preferred embodiment, the pharmaceutical preparation according to the invention is used for intranasal delivery. Stimulation of the immune system by these antigen-presenting virosome-like-particles may be due to a combination of their specific recognition by cells of the immune system, their particular character, the presentation of the protein, and the uncovering of hidden epitopes.

By 'antigens' as used herein, are meant proteins, peptides or polypeptides that have at least one hydrophilic and at least one hydrophobic moiety and that can elicit an immune response in the host whereto it is delivered. Non-limiting examples of such integral membrane proteins are membrane proteins from tumor cells, from bacteria, parasites, yeasts and the envelope of viruses. Viral membrane proteins that can be used can be derived from a wide range of viruses. These viruses include, but are not limited to: Retroviridae such as Human Immunodeficiency virus (HIV); a rubellavirus; paramyxoviridae such as parainfluenza viruses, measles mumps, respiratory syncytial virus, human metapneumovirus; flaviviridae such as yellow fever virus, dengue virus, Hepatitis C Virus (HCV), Japanese Encephalitis Virus (JEV), tick-borne encephalitis, St. Louis encephalitis or West Nile virus; Herpesviridae such as Herpes Simplex virus, cytomegalovirus, Epstein-Barr virus; Bunyaviridae; Arenaviridae; Hantaviridae such as Hantaan; Coronaviridae; Poapavaviridae such as human Papillomavirus; Rhabdoviridae such as rabies virus; Coronaviridae such as human coronavirus; a Alphaviridae, Arteriviridae, filoviridae such as Ebolavirus, Arenaviridae, poxyiridae such as smallpox virus, and African Swine Fever virus.

EXAMPLES

Example 1

Preparation of a Virosome-Like-Particle Containing the Influenza Hemagglutinin Glycoprotein Influenza virus was produced by growing virus acquired from the World Influenza Center or the American Type Tissue Culture Collection (ATCC, Rockville, Md.), using methods known to persons skilled in the art, for instance by growing the virus on embryonated eggs or in cultured cells such as PER.C6™ or MDCK cells. The virus was then purified, by density gradient ultracentrifugation, and may subsequently be inactivated by treatment with beta-propiolactone or formaldehyde according to established procedures. Inactivation is not required for this procedure, and may affect the immune response. The virus may be further purified by the resuspension of sedimented virus in 5.0 mM Hepes (pH 7.4), containing 0.15 mM NaCl and 0.1 mM EDTA (HNE-buffer), and loading this preparation atop linear 10-60% (w/v) sucrose gradients in HNE, centrifuging at 90,000×g for 36 hr at 4° C. Virus can be pooled and aliquots stored at −80° C. This additional purification step was not required for the formation of virosome-like-particles.

For reconstitution by dicaproyl-phosphatidylcholine (DCPC), formaldehyde-inactivated egg-grown influenza virus, strain X-47 (0.25 µmol phospholipid) was first sedimented by ultracentrifugation, and subsequently resuspended with 0.55 ml HNE-buffer, containing 25 mM DCPC. After a 30 min incubation at 0° C., the viral membrane was solubilized, and the nucleocapsids were removed by centrifugation for 20 min at 100,000×g at 4° C. The supernatant was used for reconstitution.

The efficiency of solubilization of the viral membrane was determined by analysis of the supernatant. The amount of soluble protein present in the supernatant was found to correspond closely to the amount of hemagglutinin (HA) protein, the major membrane protein, that was present in the virus.

For reconstitution, the supernatant was transferred to a 10,000 MW cut-off dialysis cassette ('Slide-A-Lyzer', Pierce Chemical Company, Rockford, Ill., U.S.A.) and dialyzed against 0.50 l HNE-buffer for 6 hr at 4° C., and subsequently against 0.50 l fresh HNE-buffer for 15 hr at 4° C.

To analyze the particulate character of the reconstituted material, a sample of the dialyzed material was loaded on a linear gradient of 10-50% (w/v) sucrose in HNE-buffer and centrifuged for 24 hr at 100,000×g at 4° C. (FIG. 1). After centrifugation the gradient was fractionated, and the protein and phospholipid concentrations in the fractions were determined. The largest portions of phospholipid and protein were found in the bottom of the gradient in two fractions which contained about 40% and 45% sucrose, respectively. The 45% sucrose fraction contained 24% of the phospholipid and 38% of the protein recovered in the gradient and the 40% sucrose fraction contained 32% of the phospholipid and 46% of the recovered protein. The residual phospholipid and protein were found in the remainder of the gradient. The fact that the major part of both the phospholipids and proteins co-migrated to the bottom of the gradient indicates that these were intimately associated. Previously it had been observed that mixtures of protein aggregates and lipid vesicles do not co-migrate in comparable gradients. These observations indicate that virosome-like-particles were formed.

The formation of virosomes was confirmed by electron microscopy as shown in FIG. 2. The spikes can be clearly seen to protrude from the viral membrane.

Example 2

Preparation of a Virosome-Like-Particle Containing the Semliki Forest Virus Spike Glycoproteins Semliki Forest virus, obtained from sources such as the ATCC, was produced on cell lines known in the art such as baby hamster kidney cells (BHK-21, from the ATCC) according to methods known in the art [23]. These cells were grown in Glasgow minimum essential medium, supplemented with 10% tryptose phosphate broth, 2.0 mM L-glutamine and 10% fetal bovine serum (all from GibcoBRL Life Technologies Inc., Paisley, UK). The medium was clarified by low-speed centrifugation (1,000×g) at 4° C. for 10 min, and the virus was pelleted from clarified cell-culture medium by ultracentrifugation at 100,000×g. The virus was further purified by the resuspension of sedimented virus in 6.0 mM Hepes (pH 7.4), containing 0.15 mM NaCl and 0.1 mM EDTA (HNE-buffer), and loading this preparation atop linear 10-60% (w/v) sucrose gradients in HNE, centrifuging at 90,000×g for 36 hr at 4° C. Virus was pooled and aliquots were stored at −80° C. This additional purification step was not required for the formation of virosome-like-particles and does not affect the immune response.

For reconstitution by dicaproyl-phosphatidylcholine (DCPC), the virus (0.25 µmol of phospholipid) was first sedimented by ultracentrifugation, and subsequently resuspended with 0.50 ml HNE-buffer, containing 100 mM DCPC. After a 30 min incubation at 0° C., the viral membrane was solubilized, and the nucleocapsids were removed by centrifugation for 20 min at 100,000×g at 4° C. Efficient solubilization of the virus was demonstrated by an analysis of the supernatant and pellet by SDS-PAGE chromatography as shown in FIG. 3. As shown in the figure, in the virus sample the protein bands representing E1, E2 and capsid (C) were equally intense. In the supernatant recovered after ultracentrifugation the two major bands visible represent E1 and E2, while the major protein recovered in the pellet was C.

To form virosome-like-particles, the supernatant was transferred to a 10,000 MW cut-off dialysis cassette ('Slide-A-Lyzer', Pierce Chemical Company, Rockford, Ill., U.S.A.) and dialyzed against 0.50 l HNE-buffer for 6 hr at 4° C., and subsequently against 0.50 l fresh HNE-buffer for 15 hr at 4° C.

Example 3

Membrane Fusion Activity of Influenza Virosomes

For analysis of the membrane fusion activity of the a virosome preparation, the X-47 strain of influenza virus (0.25 µmol phospholipid) was first sedimented by ultracentrifugation, and subsequently resuspended with 0.55 ml HNE-buffer, containing 25 mM DCPC. After a 30 min incubation at 0° C., the viral membrane was solubilized, and the nucleocapsids were removed by centrifugation for 20 min at 100,000×g at 4° C. The supernatant was then added to a dried thin film of 10 nmol of (1-pyrenedecanoyl)-sn-phosphatidylcholine (pyrPC) (Molecular Probes, Leiden, The Netherlands). After incubation for 20 min at 4° C., virosome-like-particles were then formed from this mixture by dialysis as described above. For the measurement of membrane fusion, the resulting virosome-like-particles were mixed with erythrocyte ghosts, prepared as described previously [25] from human red blood cells, at neutral pH (pH 7.4) at 37° C. At time 0, the medium was acidified as indicated. Fusion was monitored continuously by following the decrease of the pyrene excimer fluorescence. For comparison with the fusion activity of influenza virus, a virus sample was labeled with octadecylrhodamine (R18) as previously described [27]. The results, demonstrated in FIG. 4, clearly indicate that fusion of virosomes and virus displays the same steeps pH dependence and occurs at comparable rates. Therefore, the fusion activity of the viral spikes was conserved.

Example 4

Membrane Fusion Activity of SFV Virosomes

To prepare virosomes for the measurement of fusion activity, SFV (0.25 µmol phospholipid) was first sedimented by ultracentrifugation, and subsequently resuspended with 0.50 ml HNE-buffer, containing 100 mM DCPC. After a 30 min incubation at 0° C., the viral membrane was solubilized, and the nucleocapsids were removed by centrifugation for 20 min at 100,000×g at 4° C. The supernatant was then added to a dried thin film of 7.5 nmol of (1-pyrenedecanoyl)-sn-phosphatidylcholine (pyrPC) (Molecular Probes, Leiden, The Netherlands). After an incubation for 20 min at 4° C., the supernatant was transferred to a 10,000 MW cut-off dialysis cassette ('Slide-A-Lyzer', Pierce Chemical Company, Rockford, Ill., U.S.A.) and dialyzed against 0.50 l HNE-buffer for 6 hr at 4° C., and subsequently against 0.50 l fresh HNE-buffer for 15 hr at 4° C. Liposomes used as targets in the fusion assay were prepared from egg phosphatidylcholine (PC), phosphatidylethanolamine (PE) derived from egg PC, bovine brain SPM and cholesterol (molar ratio 1:1:1:1.5) by a freeze-and-thaw/extrusion procedure [44]. For the measurement of membrane fusion, as shown in FIG. 5, the resulting virosome-like-particles were mixed with liposomes at neutral pH 7.4, 37° C. At time 0 the medium was acidified as indicated. Fusion was continuously monitored by following the decrease of pyrene excimer fluorescence. The results indicate that efficient and rapid low-pH-dependent fusion of the virosomes with the liposomes occured.

Example 5

Immunization of Mice with Virosome-Like-Particles Containing Influenza Hemagglutinin Immunization of mice by parenteral application of virosome-like particles reconstituted by the short-chain phospholipid method was compared to immunization with a conventional influenza subunit vaccine formulation. Balb/C mice (5 animals per group) were immunized, on days 0 and 14, by intramuscular injection of 30-50 microliters of virosome-like preparation in HNE-buffer preparation, containing 5 µg of HA, derived from inactivated influenza virus (strain X-47$H_3N_2$). Blood was collected on day 21. Serum samples were frozen in liquid nitrogen and stored at −20° C. until analysis. Hemagglutination-inhibition (HI) titers were determined using guinea pig erythrocytes according to standard methodology. The results are described in Table I. It is shown that virosome-like-particles elicit a more potent virus-neutralizing antibody response than subunit antigen.

TABLE I

Hemagglutination-inhibition titers in mice after immunization with influenza virosome-like-particles or subunit antigen

| Immunogen | HI titer (±S.D.) |
|---|---|
| Subunit antigen | 96 ± 36 |
| Virosome-like-particles | 215 ± 73 |

REFERENCES

1 Ogra P. L., Faden H., Welliver R. C. (2001) Clin Microbiol Rev 14, 430-445
2 Janeway et al. (2001) Immunobiology, 5th edition, Garland Publishing, New York
3 Cox J. C, Sjolander A., Barr I. G. (1998) Adv Drug Delivery 32, 247-271
4 Lowell, G. H. et al., J Exp Med (1988) 167, 658-663
5 Almeida, J. D., Edwards, D. C., Brands, C. M. and Heath, T. D. (1975) The Lancet 699-701
6 White, J. M. (1990) Annual Review of Physiology 52, 675-697
7 Wiley, D. C. and Skehel, J. J. (1987) Annual Review of Biochemistry 56, 365-394
8 Strauss, J. H. and Strauss, E. G. (1994) Microbiological Reviews 58, 491-562
9 Stegmann, T. (1993) Journal of Biological Chemistry 268, 1716-1722
10 White, J. and Helenius, A. (1980) Proceedings of the National Academy of Sciences USA 77, 3273-3277
11 Kielian, M. C. and Helenius, A. (1984) Journal of Virology 52, 281-283
12 Phalen, T. and Kielian, M. (1991) Journal of Cell Biology 112, 615-623
13 Nieva, J. L., Bron, R., Corver, J. and Wilschut, J. (1994) EMBO Journal 13, 2797-2804
14 Corver, J., Moesby, L., Erukulla, R. K., Reddy, K. C., Bittman, R. and Wilschut, J. (1995) Journal of Virology 69, 3220-3223
15 Moesby, L., Corver, J., Erukulla, R. K., Bittman, R. and Wilschut, J. (1995) Biochemistry 34, 10319-10324
16 Wilschut, J., Corver, J., Nieva, J. L., Bron, R., Moesby, L., Reddy, K. C. and Bittman, R. (1995) Molecular Membrane Biology 12, 143-149
17 Stegmann, T., Morselt, H. W. M., Booy, F. P., van Breemen, J. F. L., Scherphof, G. and Wilschut, J. (1987) EMBO Journal 6, 2651-2659
18 Bron, R., Ortiz, A., Dijkstra, J., Stegmann, T. and Wilschut, J. (1993) Methods in Enzymology 220, 313-331
19 Stegmann, T., Schoen, P., Bron, R., Wey, J., Bartoldus, I., Ortiz, A., Nieva, J. L. and Wilschut, J. (1993) Biochemistry 32, 11330-11337
20 Schoen, P., Corver, J., Meijer, D. K. F., Wilschut, J. and Swart, P. J. (1997) Biochemical Pharmacology 53, 995-1003
21 Schoen, P., Leserman, L. and Wilschut, J. (1996) FEBS Letters 390, 315-318
22 Schoen, P., Bron, R. and Wilschut, J. (1993) Journal of Liposome Research 3, 767-792
23 Bron, R., Ortiz, A. and Wilschut, J. (1994) Biochemistry 33, 9110-9117
24 Tausk, R. J. M., Karmiggelt, J., Oudshoorn, C. and Overbeek, J. T. G. (1974) Biophysical Chemistry 1, 175-183
25 Steck, T. L. and Kant, J. A. (1974) Methods in Enzymology 31, 172-180
26 Hope, M. J., Bally, M. B., Webb, G. and Cullis, P. R. (1985) Biochimica et Biophysica Acta 812, 55-65
27 Stegmann, T. et al. (1987) The Journal of Biological Chemistry 262, 17744-17749

The invention claimed is:

1. A method for producing a virosome, comprising the steps of:
   a) contacting an intact enveloped virus with a solution containing a short-chain phospholipid, wherein the short-chain phospholipid is 1,2-dicaproyl-sn-phosphatidylcholine (DCPC) or 1,2-diheptanoyl-sn-phosphatidylcholine (DHPC);
   b) allowing solubilisation of the viral envelope of said virus, and
   c) removing said short-chain phospholipid from said solution by dialysis or filtration allowing formation of a functionally reconstituted viral envelope, wherein said functionally reconstituted viral envelope maintains membrane fusion activity.

2. A method according to claim 1 further comprising removal of viral nucleocapsid from said solution.

3. A method according to claim 1 wherein said virus is selected from the group consisting of an influenza virus, retroviridae, paramyxoviridae, flaviviridae, herpesviridae, coronaviridae, papovaviridae, rhabdoviridae, alphaviridae, arteriviridae, filoviridae, arenaviridae, and poxviridae.

4. A method according to claim 1 further comprising addition of a molecule that is not derived from said virus to said virosome.

5. A method according to claim 4 wherein said molecule comprises a lipid or a protein.

6. A method according to claim 4 wherein said molecule is amphiphilic.

7. A method according to claim 4 wherein said molecule is derived of a pathogen.

8. A method according to claim 7 wherein said pathogen is a virus, a bacterium or a parasite.

9. A method according to claim 4 wherein said molecule comprises a tumor-specific antigen.

10. A method for producing a pharmaceutical composition, said method comprising:
    a) producing a virosome comprising the steps of:
       i) contacting an intact enveloped virus with a solution containing a short-chain phospholipid, wherein the short-chain phospholipid is 1,2-dicaproyl-sn-phosphatidylcholine (DCPC) or 1,2-diheptanoyl-sn-phosphatidylcholine (DHPC);
       ii) allowing solubilisation of the viral envelope of said virus, and
       iii) removing said short-chain phospholipid from said solution by dialysis or filtration allowing formation of a functionally reconstituted viral envelope, wherein said functionally reconstituted viral envelope maintains membrane fusion activity.
    b) further comprising mixing the virosome and a pharmaceutically acceptable carrier.

11. A method according to claim 10 wherein said pharmaceutical composition comprises a vaccine.

12. A method according to claim 10 wherein said pharmaceutical composition is suitable for parenteral or mucosal application.

* * * * *